(12) United States Patent
Durst et al.

(10) Patent No.: US 6,836,532 B2
(45) Date of Patent: Dec. 28, 2004

(54) DIFFRACTION SYSTEM FOR BIOLOGICAL CRYSTAL SCREENING

(75) Inventors: Roger D. Durst, Middleton, WI (US); Bob Baoping He, Madison, WI (US)

(73) Assignee: Bruker AXS, Inc., Madison, WI (US)

( * ) Notice: Subject to any disclaimer, the term of this patent is extended or adjusted under 35 U.S.C. 154(b) by 0 days.

(21) Appl. No.: 10/118,981

(22) Filed: Apr. 9, 2002

(65) Prior Publication Data

US 2003/0147496 A1 Aug. 7, 2003

Related U.S. Application Data

(63) Continuation-in-part of application No. 09/896,824, filed on Jun. 29, 2001.

(51) Int. Cl.⁷ .......................... G01N 23/207; C30B 7/00
(52) U.S. Cl. .............................. 378/73; 378/71; 378/79; 378/80; 378/208; 117/14; 117/69; 117/85; 117/201; 117/206
(58) Field of Search ............................. 378/71, 73, 76, 378/79, 80, 208; 117/14, 68, 69, 84, 85, 201, 206, 901

(56) References Cited

U.S. PATENT DOCUMENTS

| | | | | |
|---|---|---|---|---|
| 4,634,490 A | * | 1/1987 | Tatsumi et al. | ............... 117/14 |
| 5,096,676 A | * | 3/1992 | McPherson et al. | ......... 117/206 |
| 5,221,410 A | | 6/1993 | Kushner et al. | |
| 5,419,278 A | * | 5/1995 | Carter | ......................... 117/206 |
| 5,597,457 A | | 1/1997 | Craig et al. | |
| 5,636,258 A | * | 6/1997 | Okumura et al. | ............. 378/73 |
| 5,848,124 A | * | 12/1998 | Inazuru | ...................... 378/140 |
| 6,507,636 B1 | * | 1/2003 | Lehmann | ...................... 378/79 |
| 2002/0062783 A1 | * | 5/2002 | Bray | ............................. 117/68 |
| 2002/0067800 A1 | * | 6/2002 | Newman et al. | ............. 378/73 |

* cited by examiner

Primary Examiner—Edward J. Glick
Assistant Examiner—Allen C. Ho
(74) Attorney, Agent, or Firm—Kudirka & Jobse, LLP

(57) ABSTRACT

A biological crystal formation screening apparatus uses an x-ray diffraction technique to analyze the sample containers of a sample tray for the presence of crystal formation. An x-ray source is directed toward a sample under investigation, and a two-dimensional x-ray detector is located to receive any diffracted x-ray energy. A positioning apparatus allows the different sample containers of a tray to be sequentially aligned with the source and detector, allowing each to be examined. The sample container is arranged such that a sample is located relative to the well solution so that the x-ray beam is directed to the sample without being incident on the well solution.

22 Claims, 6 Drawing Sheets

DIFFRACTION SYSTEM FOR BIOLOGICAL CRYSTAL SCREENING

RELATED APPLICATIONS

This application is a continuation-in-part of U.S. patent application Ser. No. 09/896,824, filed Jun. 29, 2001.

FIELD OF THE INVENTION

The present invention relates generally to the field of structural genomics and, more specifically, to the use of crystallography to examine protein crystals for genomic research.

BACKGROUND OF THE INVENTION

In biological research, particularly in the field of genomics, crystallography is a tool used to examine the characteristics of proteins. However, such proteins are typically developed in a liquid medium, and therefore must be crystallized in an orderly fashion before detailed crystallography techniques may be used. A typical method for crystallizing such proteins is through vapor diffusion. In a method known as the "hanging drop" method, a well solution is placed in the many separate sample wells of the sample tray. For each sample well, a drop of protein liquid is applied to a slide, which is placed over the sample well with the drop hanging down toward the well solution. Because of different relative concentrations of the well solution and the droplet solution, over time, liquid diffuses out of the droplet and into the sample well, resulting in the crystallization of the protein on the surface of the slide.

Depending on the conditions under which the crystallization process takes place, the formation of a crystal may take anywhere from hours to months. While some crystals are visible to the naked eye, the sample slides must usually be examined with a microscope one at a time to determine whether protein crystallization has taken place. Of course, for those protein samples that have not yet crystallized, the slides must be reexamined on a regular basis until the crystallization is observed. For a relatively large number of samples, this is obviously a long and labor-intensive process.

SUMMARY OF THE INVENTION

In accordance with the present invention, a screening apparatus is provided for monitoring crystal formation in a crystal growth medium that makes use of an x-ray source and detector. X-ray energy from the x-ray source is incident on a sample container and undergoes diffraction if in the presence of a crystal structure. Any such diffracted x-ray energy is detected by the x-ray detector, the output of which is indicative of the presence or absence of such a crystal structure. In this way, one may determine whether any significant crystal formation has taken place in the crystal growth medium, without the need for visual examination of the sample container. This is particularly useful for the examination of biological crystal formation common in genomics research.

In a preferred embodiment, the screening apparatus also includes a positioning apparatus for locating the sample container relative to the x-ray source and x-ray detector. The positioning apparatus has a support that is remotely movable in at least two dimensions, allowing the precise positioning of the sample container relative to the x-ray source and detector. This is particularly useful in the preferred embodiment of the invention, in which the sample container is one of a plurality of sample containers each having a separate crystal growing medium. The sample containers may be part of a contiguous array, such as in a sample tray having an array of sample wells. In such a case, the positioning apparatus may be used to move the sample containers so as to position them sequentially relative to the x-ray source and detector, thereby allowing sequential examination of the sample containers. In addition, the source and detector may be arranged to operate in reflective mode or in transmission mode. If used in transmission mode, the positioning apparatus preferably has an open section located between the source and a sample well under investigation so as to not interfere with the source x-ray energy.

The x-ray source and detector may be arranged such that the exposure of x-rays from the source covers a two-dimensional area of the sample container being examined, in particular, an area over which any significant crystal formation would be expected to appear. The detector, similarly, is a two-dimensional detector, providing simultaneous detection of x-ray energy diffracted from a similar two-dimensional region of the sample container. Therefore, a simultaneous set of pixel intensities may be collected that is indicative of any presence of crystal structures across the two-dimensional area of the sample container under investigation.

A control apparatus is preferably used to control the various aspects of the screening apparatus, including the triggering of the x-ray source and the collection and processing of data from the detector. The control apparatus may also be used to control the positioning apparatus to synchronize the alignment of the various sample containers in an array with the operation of the x-ray source and detector. In this way, a the system may be used to automatically analyze the entire array of sample containers to determine which, if any, show the formation of any significant crystal structure.

In addition to the structural aspects of the invention, various techniques are also provided that may be used to evaluate the intensity data from the pixels of the detector to make a determination of whether or not a crystal is present. One such technique involves determining the number of pixels having an intensity level exceeding a minimum pixel intensity level and comparing that number to a predetermined minimum number selected as being indicative of the presence of said crystal structure. In another method, the outputs from a predetermined number of pixels having the highest intensity levels are averaged and compared to an overall average intensity value of all the pixels. In yet another method, the pixel intensity values that are indicative of the presence of a crystal peak in the detected spectrum are isolated and integrated. This integrated crystal peak intensity is then compared to an integrated intensity of all the detector pixels.

A particular type of sample container may be used with the present invention to minimize scattering from the well solution despite the x-ray source being on one side of the container while the detector is on the opposite side. The solution is retained within a reservoir region of the container, and the sample is located at a sample location. However, the sample location is arranged relative to the reservoir such that a beam of x-ray energy travels from the x-ray source to the sample location without being incident on the well solution.

In a first version of this embodiment, the sample is located on a platform and is retained there under the force of gravity. Although the well solution resides at a lower point in the sample container than the sample, a region below the platform is devoid of well solution, and the x-ray beam passes through this region and through the platform to reach the sample. The platform is preferably smaller within a portion of it through which a maximum portion of x-ray energy passes (typically in the center), than in surrounding portions. The surface of the platform upon which the sample resides may be concave, as may be the opposite surface. Preferably, the material of the platform is mostly or entirely amorphous.

In another variation of this embodiment, the sample resides on the underside of a surface within the sample container under the force of surface tension. Again, despite the well solution being at a lower point within the sample container, a region below the sample is clear of any well solution. Preferably, a baffle surrounds this portion of the container, and excludes the well solution therefrom. Although the well solution is still in the same enclosed space with the sample, an x-ray beam may be directed through the portion of the container below the sample without encountering any well solution.

BRIEF DESCRIPTION OF THE DRAWINGS

The above and further advantages of the invention may be better understood by referring to the following description in conjunction with the accompanying drawings in which.

DETAILED DESCRIPTION

Figure 1:
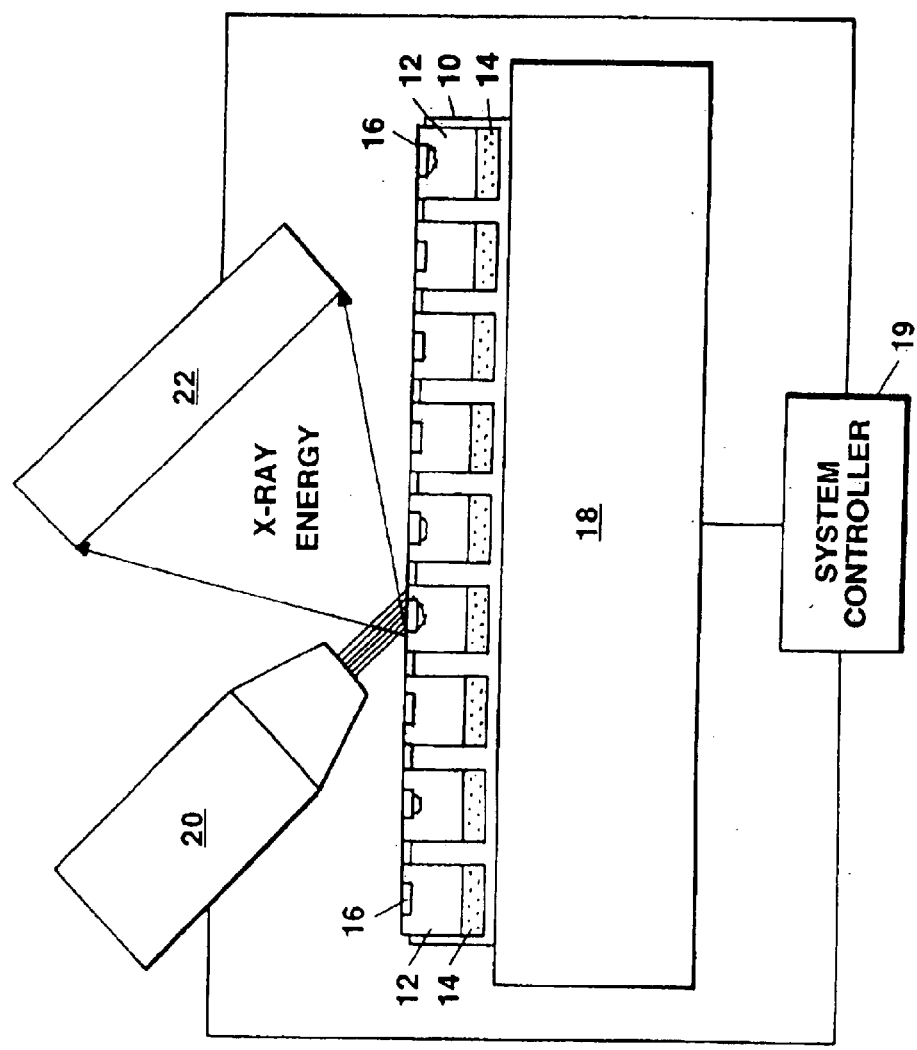
FIG. 1 is a schematic side view of a screening apparatus according to the present invention.

Shown in FIG. 1 is an x-ray screening apparatus that may be used to identify the crystallization of protein samples in a sample tray 10. In the figure, the sample tray 10 is shown in a cross-sectional side view, so that the contents of one row of sample wells 12 are apparent. Contained within each of the wells 12 is a well solution 14 that induces vapor diffusion from a sample drop located in the underside of a slide (or mylar film) 16 covering the top of the well. The process of vapor diffusion is well known in the art, and will not be repeated in any significant detail herein. However, in the present embodiment, rather than use visual inspection to determine when crystallization has occurred, the samples are examined using a diffraction-based technique.

In the embodiment of FIG. 1, the sample tray is mounted on a translation table 18 that is adjustable in three dimensions. The translation table allows the sample tray to be repositioned within a three dimensional area in order to align and realign the sample wells as desired. Control of the movement of the translation table 18 is preferably automated, and responsive to a control program for examining the samples. Movement of the translation table 18, and thereby the sample tray 10, allows it to be repositioned relative to x-ray source 20 and two-dimensional x-ray detector 22.

In the preferred embodiment, x-ray source 20 is a sealed tube or a rotating target generator that produces x-ray radiation in a wavelength range of approximately 0.5 to 2.3 angstrom. The source 20 also includes appropriate x-ray optics to condition the x-ray beam into a specified beam size, spectrum and beam profile. The detector 22 is any of a number of known two-dimensional x-ray detectors that can simultaneously detect the intensity of x-ray energy with a number of pixels across a two-dimensional area. In operation, each sample well is scanned one at a time. The scanning operation is controlled by a system controller 19 that controls the firing of the x-ray source 20, the data collection from detector 22 and movement of translation table 18. Preferably, the controller runs an automatic scanning routine that provides sequential scanning of all (or selected) sample wells, and corresponding data collection and processing. Control apparatus such as these are known in other fields, and are easily adaptable to the present invention by one skilled in the art. In operation, the translation table 18 moves the tray so that a sample well 12 to be examined is in the path of an x-ray beam from the source 20. The incident x-rays pass through the coverslips or mylar film and are incident upon the hanging droplet within the sample well. The cross-sectional area of the incident beam is large enough that a single exposure will reach any part of the well in which a crystal might form. If a crystal is present, it diffracts the x-rays from source 20 in the direction of the detector 22, where x-ray intensities are detected across the detector surface.

Figure 2:
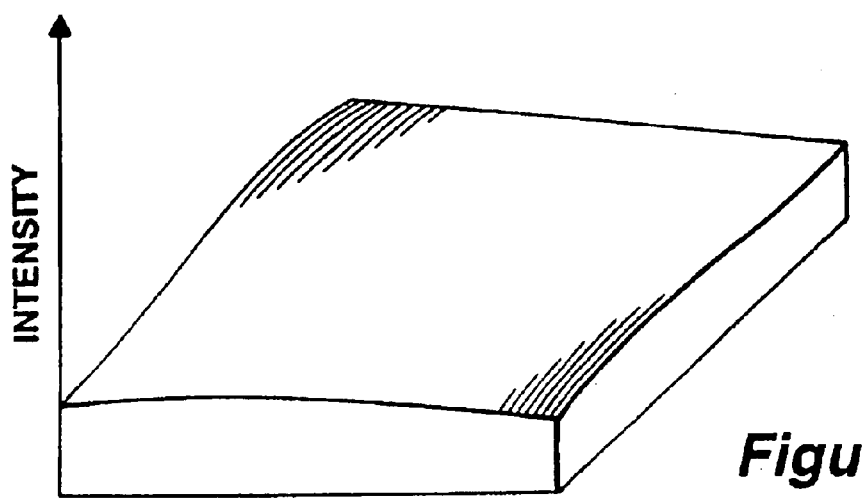
FIG. 2 is a graphical view of a two-dimensional set of x-ray intensities resulting from x-ray scattering from an amorphous surface.

As each sample well is scanned, a data frame is collected for it that is representative of two-dimensional distribution of x-ray intensities across the detector surface. Based on the content of this data frame, a determination may be made regarding the degree to which any crystal structure has formed in the sample well under investigation. Shown in FIG. 2 is a graphical depiction of the pixel intensity distribution in a data frame for which there is no significant crystal formation. Materials surrounding the sample material, such as the crystallization plate, coverslips or mylar film and the liquid are amorphous, so that the x-rays scattered by them are randomly distributed. This results in a spectrum as shown in FIG. 2, in which there is a relatively consistent distribution of x-ray energy across the two-dimensional space.

Figure 3:
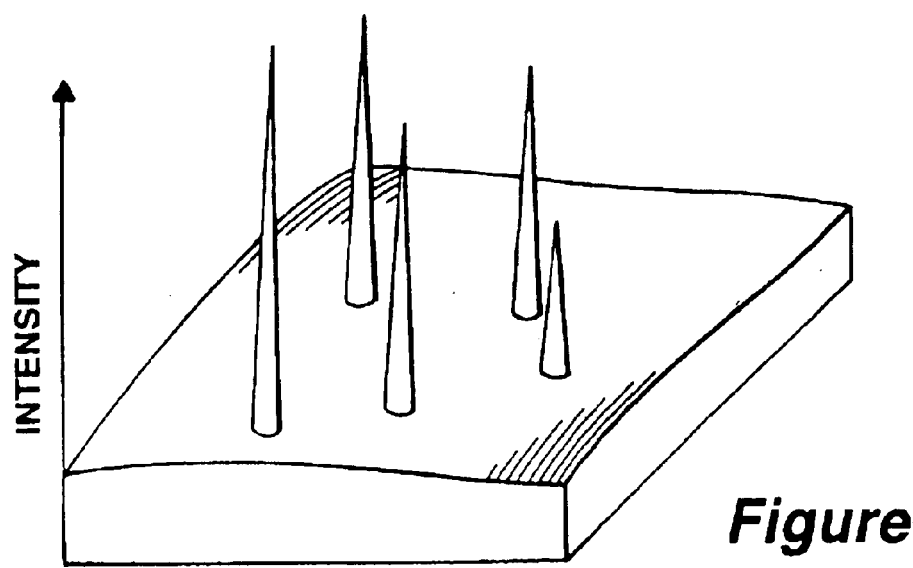
FIG. 3 is a graphical view of a two-dimensional set of x-ray intensities resulting from diffraction from a crystal structure and background scattering from amorphous materials.

When there is a significant degree of crystallization in a sample well, the crystal will diffract x-rays toward the detector 22. The diffracted x-rays form sharp intensity peaks much more intense than the background caused by scattering from amorphous materials. The particular crystallinity condition within each screening spot can be determined by the number and intensity of the peaks. An example of such a spectrum is depicted graphically in FIG. 3. As shown, within the background noise caused by the scattering from amorphous materials are several distinct diffraction peaks. The presence of these peaks may be used as part of an automated analysis program for screening the protein samples.

Figure 4:
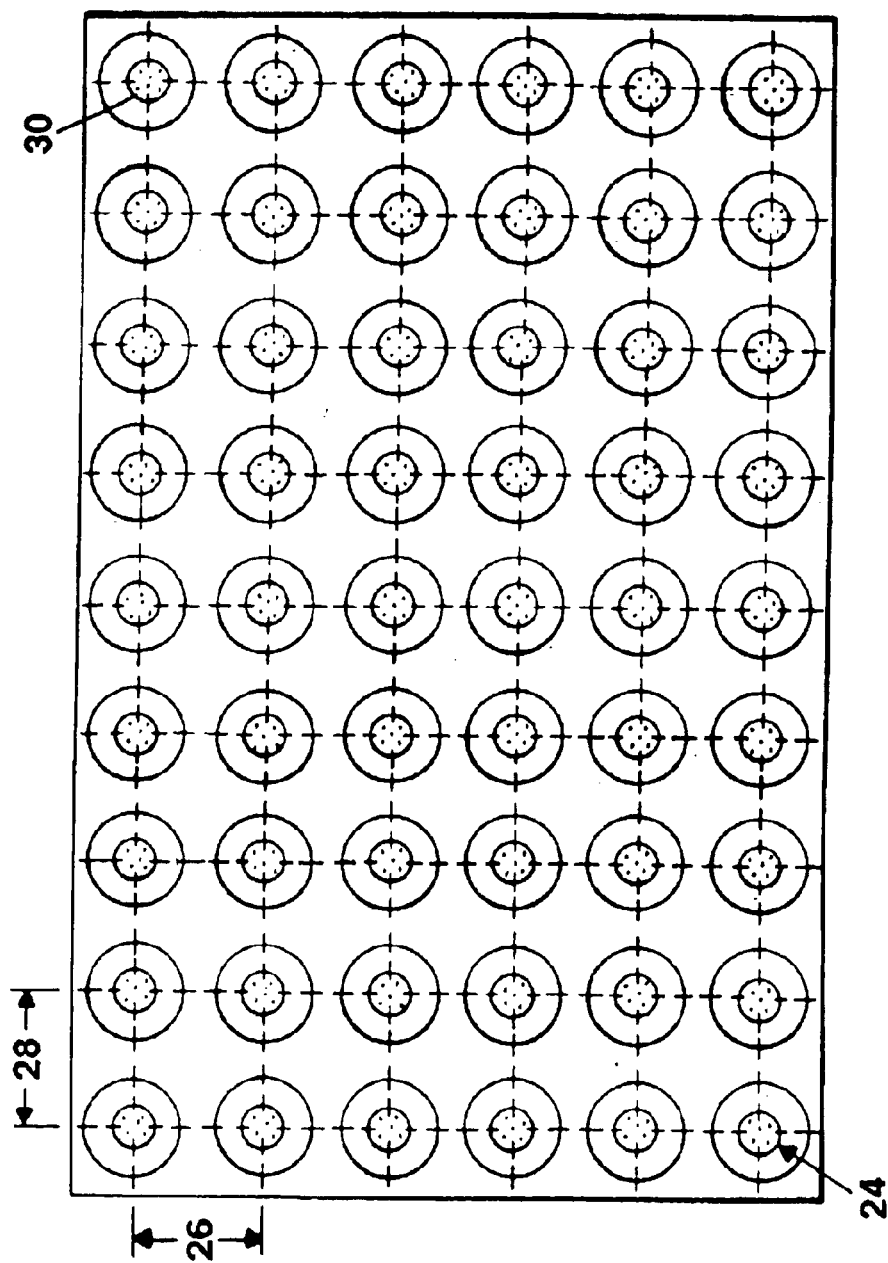
FIG. 4 is a schematic top view of a sample tray having an array of sample wells.

Shown in FIG. 4 is a schematic top view of a sample tray having a 6×9 array of sample wells. Those skilled in the art will recognize that this particular number of sample wells is for illustrative purposes only, and the actual sample tray may have any number of sample wells, and will likely have many more than are shown. From this figure, it may be understood that the translation table 18 shown in FIG. 1 may be used to move the sample so as to sequentially align the sample wells with the x-rays from source 20. The instrument center is defined by the crossing point of the incident x-ray beam and a center line of the detector. The system automatically and sequentially moves the tray so that the location of each droplet is sequentially moved to the instrument center. As each of the sample wells is aligned with the source, a data set is collected with the detector 22, and stored for analysis purposes. Using an arrangement as shown in FIG. 4, the progress in the movement of the tray may be broken down by a series of steps in two dimensions. Once the tray is located relative to a starting location, such as point 24, oriented at the instrument center, subsequent movements of the tray may be a series of predetermined steps, such as an x-dimension step 26, or a y-dimension step 28. With each step, a scan is performed of the sample well located at the new location, and the movement continues until an end location, such as location 30, is reached. At this point data collection is complete. Of course, those skilled in the art will recognize that any desired scanning pattern may be used as necessary, and the provision of a user interface that allows custom table movement is fully anticipated.

Once the desired droplet scan data is collected, it must be analyzed to determine a degree of crystallization in each of the sample wells being examined. The scanning portion of the invention may be used with any desired data analysis techniques. However, several possible techniques are disclosed herein.

Figure 5:
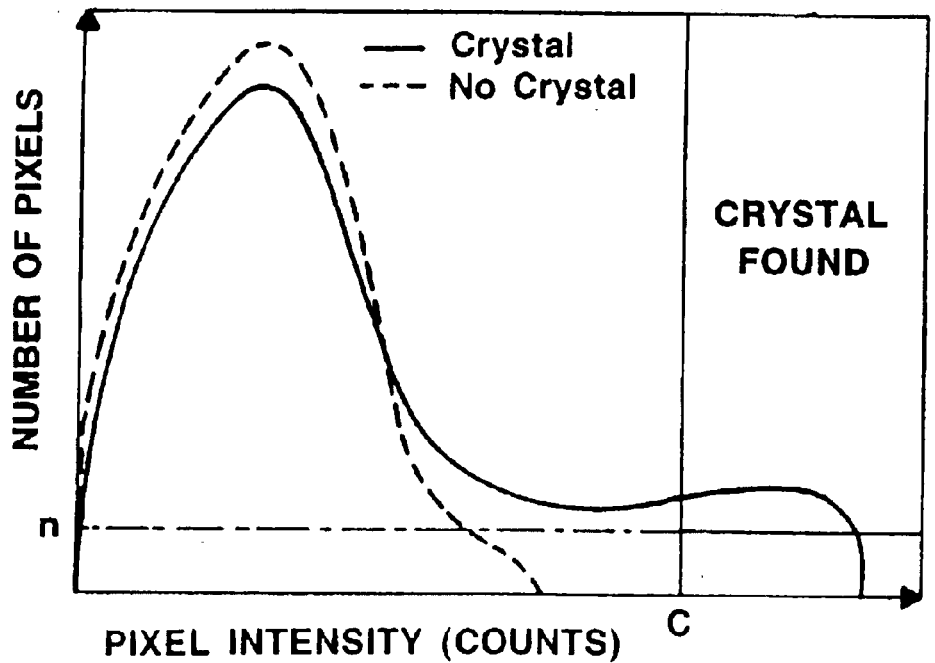
FIG. 5 is a graphical view of an absolute pixel intensity method of determining the presence of a crystal structure from a two-dimensional set of intensity data produced with a screening apparatus according to the present invention.

A first method of crystal peak identification may be referred to as the "absolute pixel intensity" method. The two-dimensional detector 22 has a given number of detection pixels, each of which detects a particular x-ray intensity each ti e a sample well is scanned. If pixel intensity is identified by a finite number of intensity levels, called "pixel counts," then a data set may be collected that correlates each pixel with a corresponding pixel count. A determination of crystal presence may then be based on meeting a threshold number of pixels having a minimum intensity level. That is, the presence of a crystal will be assumed if at least a minimum number of pixels n have at least a minimum pixel count c. A graphical interpretation of this method is depicted in FIG. 5. In this figure, the horizontal axis represents pixel count while the vertical axis represents a number of pixels for a corresponding pixel count The dashed line in the figure depicts the outcome if no crystal peaks are detected. As shown, none of the pixels register the minimum pixel count c, and a determination is therefore made that no significant crystallization has occurred at this droplet site. The solid line in the figure depicts the outcome when a sufficient number of crystal peaks are detected. As shown, the resulting curve includes more than n pixels with a minimum pixel count of c, and so a determination is made that sufficient crystallization has occurred at this site.

Another method of identifying crystal formation may be referred to as the "Relative Pixel Intensity" method. It relies on measuring the intensity of the brightest pixels relative to the average pixel intensity. In this embodiment, a predetermined number n of pixels are selected for having the highest intensity, and the average intensity $I_n$ of these n pixels is compared to the average intensity $I_o$ of all the pixels. If the ratio of the intensity of the high intensity pixels to the average pixel intensity is at least a predetermined value k, than sufficient crystallization is deemed to have occurred. The corresponding conditions may therefore be represented as follows:

If $I_n/I_o \geq k$, crystal is found

If $I_n/I < k$, no crystal is found

Figure 6:
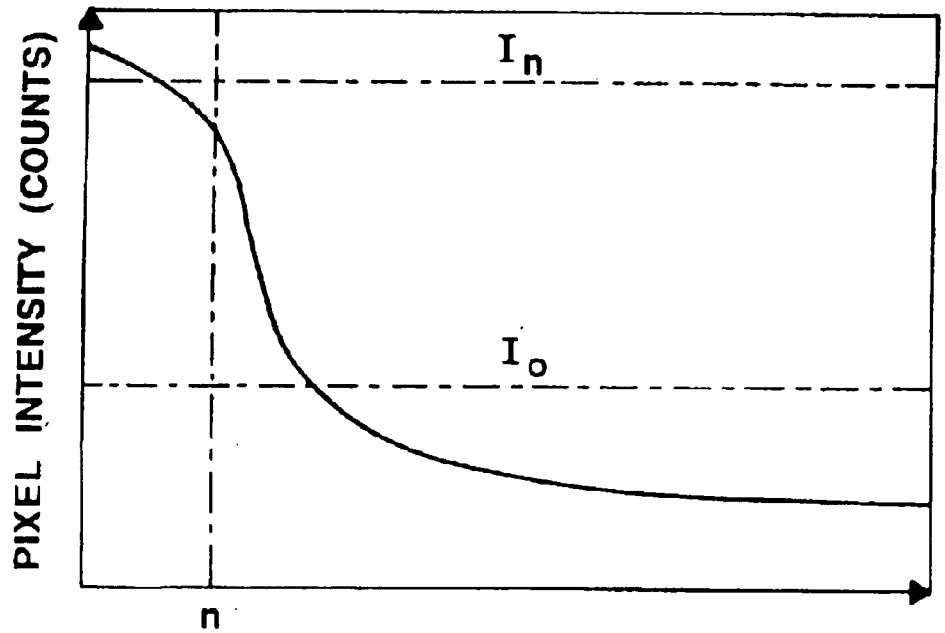
FIG. 6 is a graphical view of an relative pixel intensity method of determining the presence of a crystal structure from a two-dimensional set of intensity data produced with a screening apparatus according to the present invention.

The graphical representation of FIG. 6 shows the relative difference between the intensity averages $I_n$ and $I_o$ in a depiction of the pixel intensities arranged from highest to lowest along the horizontal axis.

Yet another method of determining the presence of crystallization may be referred to as "integrated peak intensity." This method recognizes that, when crystallization is present, there is a wide intensity difference between the sharp peaks resulting from the crystal diffraction, and the background intensity due to amorphous scattering. Certain known mathematical models are available by which the pixel data from the diffraction peaks may be separated from the pixel data from the background. Once separated, the integrated intensities for all of the crystal peaks may be compared to the total integrated intensity in the data frame. If a ratio of the integrated intensity ($I_c$) of the crystal peaks to the integrated intensity of the entire data frame ($I_t$) exceeds a predetermined value p, then sufficient crystallization is deemed to have occurred. This relationship may therefore be represented as follows:

If $I_c/I_t \geq p$, crystal is found

If $I_c/I_t < p$, no crystal is found

Those skilled in the art will recognize that many different criteria may be used to determine the presence of sufficient crystallization once the data from the detector pixels is collected. The particular method of determination may be customized to the systems and experiments of particular users.

While the embodiment of FIG. 1 demonstrates the use of the screening technique of the present invention using a system in "reflection mode," it is also possible to use a "transmission mode" arrangement. Such an arrangement is shown schematically in FIG. 7. Also demonstrated in this figure is the use of the present invention with the "sitting drop" type of vapor diffusion. Whereas the "hanging drop" method has the sample solution droplet positioned on the underside of a slide or other covering over the sample well, the "sitting drop" method locates the droplet on a separate platform elevated above the well solution 114. However, it should be noted that the present invention may be used in either reflection mode or transmission mode with either of the hanging drop or sitting drop arrangements.

Figure 7:
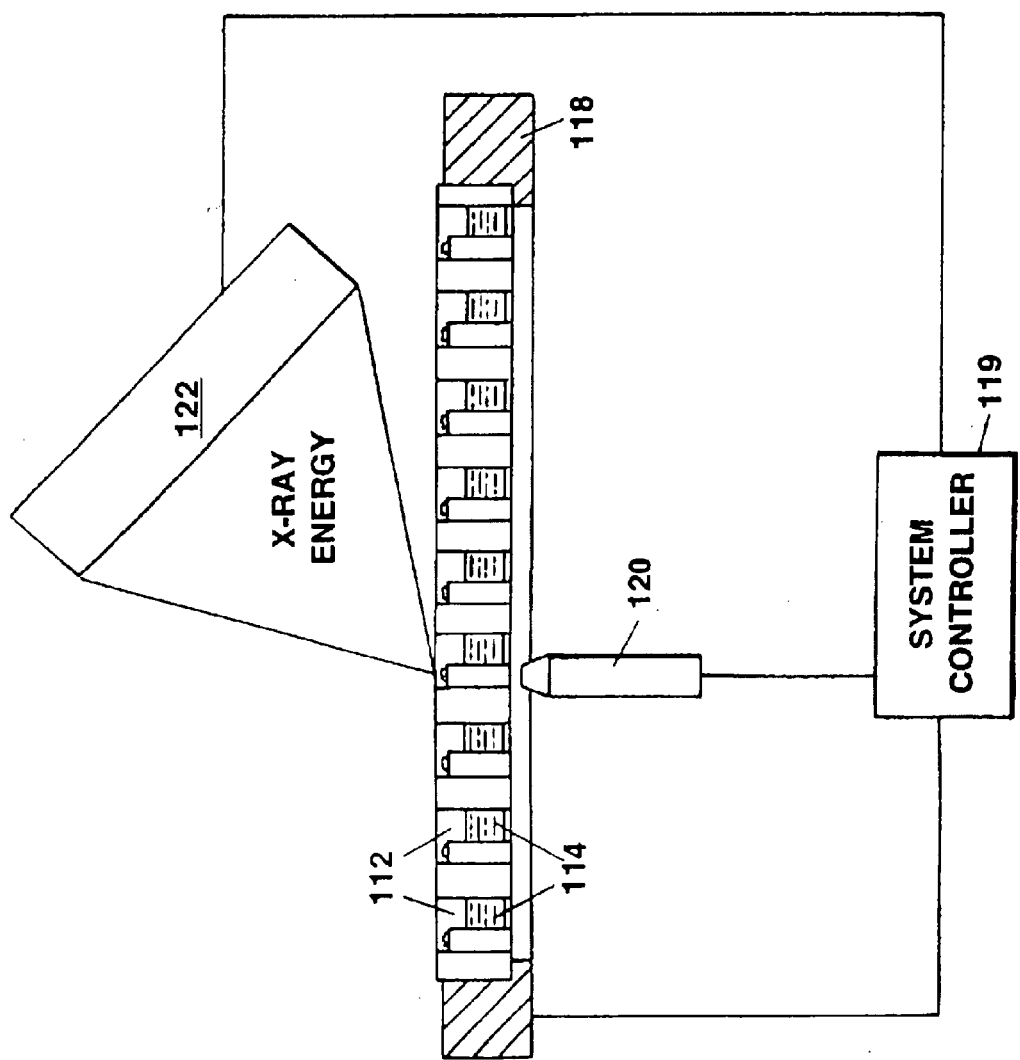
FIG. 7 is a schematic view of an alternative embodiment of the invention in which transmission mode x-ray diffraction is used with a sitting drop sample well arrangement

In the embodiment of FIG. 7, an x-ray source 120 is located to the opposite side of the sample tray from a detector 122. At least the relevant portions of the sample tray are amorphous and effectively transparent to x-ray energy so that the x-ray energy from source 120 interacts with the protein sample in the well under investigation. The translation table 118 shown in the embodiment of FIG. 7 has a cutaway portion beneath the sample wells, and the sample tray is supported along its edges. This avoids the obstruction of the source 120 by the translation table. However, those skilled in the art will recognize that a different translation table could be used as long as only x-ray transparent material separated the source 120 and the wells 112.

When there is a significant degree of crystallization in a sample well 112, the crystal will diffract x-rays toward the detector 122. The diffracted x-rays form sharp intensity peaks much more intense than the background caused by scattering from amorphous materials. This diffraction spectrum is similar to that developed when using the invention in reflection mode, but the relative diffraction angles for the wavelengths being detected are obviously different in the two arrangements. In each case, the detected wavelength peaks will depend on the relative orientation of the components, the material under investigation and the x-ray wavelengths from the source 120. As in the embodiment of FIG. 1, it is preferred that the functions of the system, including operation of the x-ray source, movement of the translation table, and collection and processing of data from the detector 122 are coordinated by a system controller 119. Naturally, other uses of the present invention that vary from the embodiments shown are anticipated.

Figure 8:
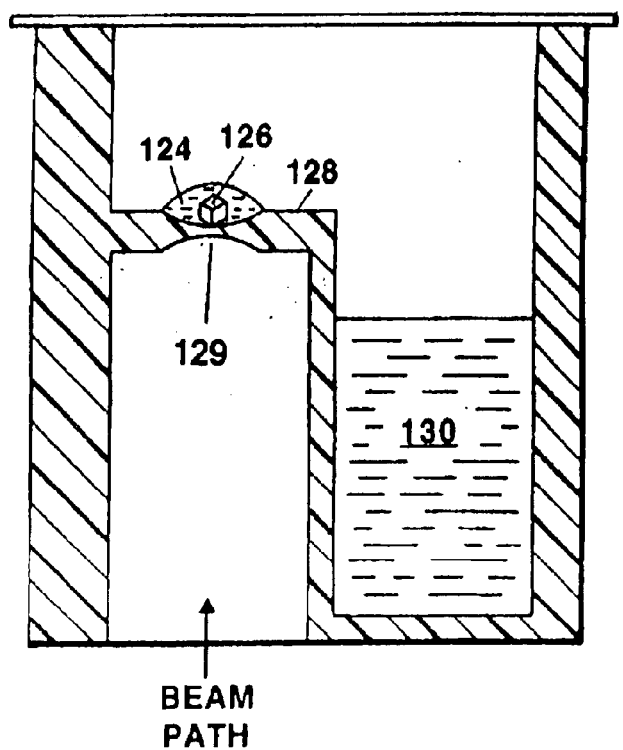
FIG. 8 is a schematic view of a sample container for a sitting drop configuration that allows an x-ray beam to be directed to the underside of a platform on which the drop resides without encountering any well solution.
Figure 9:
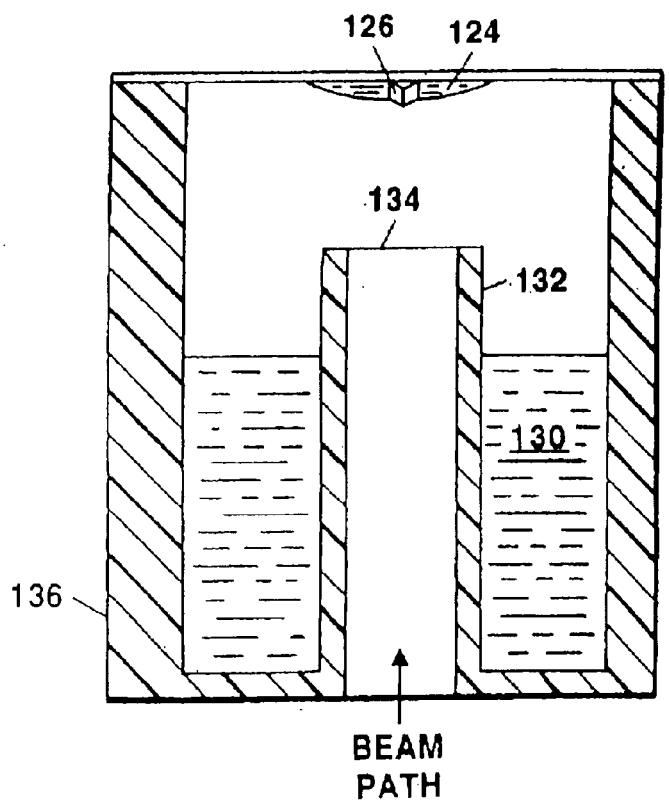
FIG. 9 is a schematic view of a sample container for a hanging drop configuration that allows an x-ray beam to be directed to the sample from an underside of the sample container without encountering any well solution.

As mentioned above, in each embodiment it is desirable to have the materials of the tray be amorphous so as to minimize the resulting scattering of the beam from the x-ray source. It is also desirable to minimize the amount of material through which the x-ray beam must pass in order to reach the sample. To this end, several alternative sample well embodiments are shown in FIGS. 8 and 9. Shown in FIG. 8 is a sample well that may be used in connection with the sitting drop type configuration. In this embodiment, a sample drop 124 containing a sample material 126 to be crystallized rests on a platform 128. Those skilled in the art will recognize that the drawing figure is not necessarily to scale, and that the sample representation is schematic for descriptive purposes only. In an adjacent portion of the sample well is a reservoir containing a well solution, as in the other embodiments. In this case, however, the platform 128 of the sample well is tapered inward such that its thickness in a plane perpendicular to the beam path is much less toward the middle of the platform than at the edges. As the source x-ray beam is directed to the middle of the platform, it passes through the thinnest region of the platform. Thus, the amount of scatter from the interaction with the platform material is minimized. Moreover, in the preferred version of this embodiment, the top of the platform is concave, so that the sample droplet settles into the cavity it forms. This helps to ensure that a high concentration of the sample material resides in the portion of the platform through which the beam is focused.

Shown in FIG. 9 is another alternative configuration for a sample well 136 that may be used with the present invention. In this embodiment, the hanging drop method is used with an x-ray source that is located to the opposite side the sample tray from a detector. The system configuration is like that of FIG. 7, except that the well supports a hanging drop rather than a sitting drop. To accomplish this with little scattering, the sample well is provided with an inner baffle 132 that provides a region through the center of the sample well that is free of well solution 130. FIG. 9 is a cross-section, and may be, for example, cylindrical in shape with a cylindrical baffle 132, although those skilled in the art will recognize that the baffle may be other shapes as long as it keeps the well solution away from the beam path. The well solution resides to the outside of the baffle, but still provides the necessary vapor diffusion, while not interfering with the x-ray beam, which might otherwise cause scattering. The top 134 of the baffle may be open to the rest of the sample well, while the bottom of the well may be covered with a sealing material, such as a foil. Alternatively, the top of the baffle may be covered by a non-scattering sealing material to prevent any of the well solution from splashing into the inner region of the baffle.

While the invention has been shown and described with reference to a preferred embodiment thereof, those skilled in the art will recognize that various changes in form and detail may be made herein without departing from the spirit and scope of the invention as defined by the appended claims.

What is claimed is:

1. A sample container for containing a sample during monitoring of crystal formation in a crystal growth medium by transmission of x-ray energy from an x-ray source on a first side of the container to he sample, presence of crystalline material resulting in diffraction of the x-ray energy toward a detector located on a second side of the container opposite the first side, the sample container comprising:
   a reservoir region within the container in which a well solution may be located for inducing evaporation of a liquid portion of the sample by vapor diffusion; and
   a platform within the container upon which the sample resides during monitoring under the force of gravity, wherein the reservoir region and the platform are arranged such that a beam of said x-ray energy travels from the x-ray source through the platform to the sample location without being incident on the well solution, the platform being physically separated from the first side of the container such that the x-ray beam passes through a region of the container having no solid material prior to encountering the platform.

2. A sample container according to claim 1 herein a dimension of the platform perpendicular to a primary direction of travel of the x-ray energy is smaller within a portion of the platform through which a maximum amount of x-ray energy passes than in surrounding portions of the platform.

3. A sample container according to claim 1 wherein a surface of the platform upon which the sample resides is concave.

4. A sample container according to claim 1 wherein the platform comprises primarily amorphous material.

5. A sample container for containing a sample during monitoring of crystal formation in a crystal growth medium by transmission of x-ray energy from an x-ray source on a first side of the container to the sample, presence of crystalline material resulting in diffraction of the x-ray energy toward a detector located on a second side of the container opposite the first side, the sample container comprising:
   a reservoir region within the container in which a well solution may be located for inducing evaporation of a liquid portion of the sample by vapor diffusion; and
   a sample location within the container in which the sample is retained during monitoring, wherein the reservoir region and the sample location are arranged such that a beam of said x-ray energy travels from the x-ray source to the sample location without being incident on the well solution wherein the sample resides on a platform within the container under the force of gravity and a surface of the platform opposite the surface upon which the sample resides is concave.

6. A sample container for containing a sample during monitoring of crystal formation in a crystal growth medium by transmission of x-ray energy from an x-ray source on a first side of the container to the sample, presence of crystalline material resulting in diffraction of the x-ray energy toward a detector located on a second side of the container opposite the first side, the sample container comprising:

a reservoir region within the container in which a well solution may be located for inducing evaporation of a liquid portion of the sample by vapor diffusion; and a sample location at which the sample resides on the underside of a surface within the sample container under the force of surface tension, the sample location being aligned with a hollow baffle surrounding an x-ray portion of the container through which the x-ray energy passes, the baffle segregating the well solution from the x-ray portion such that said x-ray energy travels from the x-ray source through the hollow baffle to the sample location without being incident on the well solution.

7. A screening apparatus for use in monitoring crystal formation in a liquid sample, the apparatus comprising:

an x-ray source that outputs x-ray energy that is incident on the sample and that undergoes diffraction in the presence of a crystal structure;

a sample container within which the sample may be located, the sample container including a reservoir region in which a well solution may be located for inducing evaporation of a liquid portion of the sample by vapor duffusion and a sample location within the container including a platform upon which the sample is retained during monitoring under the force of gravity, wherein the reservoir region and the sample location are arranged such that a beam of said x-ray energy travels from the x-ray source through the platform to the sample location without being incident on the well solution, the x-ray source directing x-ray energy toward a first side of the sample container and the platform being physically separated from said first side of the container such that the x-ray beam passes through a region of the container having no solid material prior to encountering the platform; and an x-ray detector that receives x-ray energy diffracted from said crystal structure and provides a signal indicative of the presence of the crystal structure in the sample container.

8. A screening apparatus according to claim 7 further comprising a positioning apparatus for positioning the sample container relative to the x-ray source and the x-ray detector.

9. A screening apparatus according to claim 8 wherein the positioning apparatus comprises a support that is remotely movable in at least two dimensions.

10. A screening apparatus according to claim 8 wherein the sample container is a first sample container and wherein the apparatus is arranged to operate on a plurality of sample containers each representing a separate crystal growing medium.

11. A screening apparatus according to claim 10 wherein the sample containers are all part of a contiguous sample array and wherein the positioning apparatus is capable of moving the sample array so as to sequentially position the sample containers relative to the x-ray source and x-ray detector to allow sequential examination of the sample containers.

12. A method of monitoring of crystal formation in a crystal growth medium by transmission of x-ray energy from an x-ray source to a sample under test, presence of crystalline material in the sample resulting in diffraction of the x-ray energy toward a detector located on a second side of the container opposite the first side, the method comprising:

providing a sample container having a reservoir region in which a well solution may be located that is capable of inducing evaporation of a liquid portion of the sample by vapor diffusion; and locating a sample on a platform within the container such that the platform and reservoir are arranged so that a beam of said x-ray energy travels from the x-ray source through the platform to the sample without being incident on the well solution, the platform being physically separated from the first side of the container such that the x-ray beam passes through a region of the container having no solid material prior to encountering the platform.

13. A method according to claim 12 wherein dimension of the platform perpendicular to a primary direction of travel of the x-ray energy is smaller within a portion of the platform through which a maximum amount of x-ray energy passes than in surrounding portions of the platform.

14. A method according to claim 12 wherein surface of the platform upon which the sample resides is concave.

15. A method according to claim 12 wherein the platform comprises primarily amorphous material.

16. A method of monitoring of crystal formation in a crystal growth medium by transmission of x-ray energy from an x-ray source to a sample under test, presence of crystalline material in the sample resulting in diffraction of the x-ray energy toward a detector located on a second side of the container opposite the first side, the method comprising:

providing a sample container having a reservoir region in which a well solution may be located that is capable of inducing evaporation of a liquid portion of the sample by vapor diffusion; and locating a sample at a sample location within the container such that the sample location and reservoir are arranged so that a beam of said x-ray energy travels from the x-ray source to the sample location without being incident on the well solution wherein the sample resides on a platform within the container under the force of gravity and a surface of the platform opposite the surface upon which the sample resides is concave.

17. A method of monitoring crystal formation in a crystal growth medium by transmission of x-ray energy from an x-ray source to a sample under test, presence of crystalline material in the sample resulting in diffraction of the x-ray energy toward a detector located on a second side of the container opposite the first side, the method comprising:

providing a sample container having a reservoir region in which a well solution may be located that is capable of inducing evaporation of a liquid portion of the sample by vapor diffusion; and locating the sample at a sample location on the underside of a surface within the sample container under the force of surface tension, the sample location being aligned with a hollow baffle surrounding an x-ray portion of the container through which the x-ray energy passes, the baffle segregating the well solution from the x-ray portion such that said x-ray energy travels from the x-ray source through the hollow baffle to the sample location without being incident on the well solution.

18. A screening apparatus for use in monitoring crystal formation in a liquid sample, the apparatus comprising:

an x-ray source that outputs x-ray energy that is incident of the sample and that undergoes diffraction in the presence of a crystal structure;

a sample container within which the sample may be located, the sample container including a reservoir region in which a well solution may be located for inducing evaporation of a liquid portion of the sample by vapor diffusion and a sample location within the container on the underside of a surface at which the sample is retained under the force of surface tension, the sample location being aligned with a hollow baffle surrounding an x-ray portion of the container through which the x-ray energy passes, the baffle segregating the well solution from the x-ray portion such that said x-ray energy travels from the x-ray source through the hollow baffle to the sample location without being incident on the well solution; and an x-ray detector that receives x-ray energy diffracted from said crystal structure and provides a signal indicative of the presence of the crystal structure in the sample container.

19. A screening apparatus according to claim 18 further comprising a positioning apparatus for positioning the sample container relative to the x-ray source and the x-ray detector.

20. A screening apparatus according to claim 19 wherein the positioning apparatus comprises a support that is remotely movable in at least two dimensions.

21. A screening apparatus according to claim 19 wherein the sample container is a first sample container and wherein the apparatus is arranged to operate on a plurality of sample containers each representing a separate crystal growing medium.

22. A screening apparatus according to claim 21 wherein the sample containers are all part of a contiguous sample array and wherein the positioning apparatus is capable of moving the sample array so as to sequentially position the sample containers relative to the x-ray source and x-ray detector to allow sequential examination of the sample containers.

* * * * *